(12) United States Patent
Maxey et al.

(10) Patent No.: US 7,358,275 B2
(45) Date of Patent: Apr. 15, 2008

(54) INTERNAL 1,15-LACTONES OF FLUPROSTENOL AND RELATED PROSTAGLANDIN F2A ANALOGS AND THEIR USE IN THE TREATMENT OF GLAUCOMA AND INTRAOCULAR HYPERTENSION

(75) Inventors: Kirk M. Maxey, Fort Collins, CO (US); Michelle L. Stanton, Ann Arbor, MI (US)

(73) Assignee: Cayman Chemical Company, Ann Arbor, MI (US)

( * ) Notice: Subject to any disclaimer, the term of this patent is extended or adjusted under 35 U.S.C. 154(b) by 67 days.

(21) Appl. No.: 11/353,808

(22) Filed: Feb. 14, 2006

(65) Prior Publication Data

US 2006/0172985 A1    Aug. 3, 2006

Related U.S. Application Data

(63) Continuation of application No. 09/776,574, filed on Feb. 1, 2001, now abandoned.

(60) Provisional application No. 60/179,508, filed on Feb. 1, 2000.

(51) Int. Cl.
*A61K 31/365* (2006.01)
*C07D 313/00* (2006.01)

(52) U.S. Cl. .................. 514/449; 549/200; 549/263; 549/271; 514/450

(58) Field of Classification Search ............... 549/200, 549/263, 271; 514/449, 450
See application file for complete search history.

(56) References Cited

U.S. PATENT DOCUMENTS

| | | | |
|---|---|---|---|
| 4,025,516 A | | 5/1977 | Razdan et al. |
| 4,032,543 A | * | 6/1977 | Bundy ................. 549/267 |
| 4,045,449 A | | 8/1977 | Bundy |
| 4,049,648 A | * | 9/1977 | Bundy ................. 549/267 |
| 4,049,678 A | | 9/1977 | Peterson |
| 4,116,979 A | | 9/1978 | Razdan et al. |
| 4,599,353 A | | 7/1986 | Bito |
| 5,665,773 A | | 9/1997 | Klimko et al. |

FOREIGN PATENT DOCUMENTS

| | | |
|---|---|---|
| EP | 0 639 563 A2 | 2/1995 |
| GB | 1 554 -26 | 10/1979 |
| JP | 52 1034 | 1/1977 |

OTHER PUBLICATIONS

Peterson et al (1978): STN International HCAPLUS database, Columbus (Ohio), accession No. 1978:50373.*
Jones et al (1980): STN International HCAPLUS database, Columbus (Ohio), accession No. 1980-135245.*
Fürstner, Alois and Grela, Karol; Ring-Closing Alkyne Metathesis: Application to the Stereoselective Total Synthesis of Prostaglandin E2-1,15-Lactone; Angew. Chem. Int. Ed. 39; No. 7; pp. 1234-1236; 2000.
Linden, Christina and Alm, Albert; Prostaglandin Analogues in the Treatment of Glaucoma; Drugs & Aging; 14(5); pp. 387-398; May 1999.
Monograph 4231; The Merck Index; 12th Ed.; p. 711; 1996.
Monograph 5387; The Merck Index; 12th Ed.; pp. 918-919; 1996.
Monograph 8065; The Merck Index; 12th Ed.; p. 1354; 1996.
NDA 21-214 for RESCULA Ciba Vision; pp. 1-6.
Oates, John A., et al; Clinical Implications Of Prostaglandin And Thromboxane A2 Formation (First of Two Parts); New England J. Med.; vol. 319, No. 11; pp. 689-698; Sep. 15, 1988.
Oates, John A., et al; Clinical Implications Of Prostaglandin And Thromboxane A2 Formation (Second of Two Parts); New England J. Med.; vol. 319, No. 12; pp. 761-767; Sep. 22, 1988.
Bundy, Gordon L., et al; Synthesis and Biological Activity of Prostaglandin Lactones; Journal of Medicinal Chemistry; vol. 26, No. 8; pp. 1089-1099; Aug. 1983.
Prostaglandin Lactones; Chemical Abstracts Service; Upjohn Co.; USA, database accession No. 88:104768 XP002166932 re: JP 52-001034 A (Jan. 6, 1977).

* cited by examiner

*Primary Examiner*—Golam M. M. Shameem
(74) *Attorney, Agent, or Firm*—Steven W. Hays, Esq.; Dickinson Wright PLLC

(57) ABSTRACT

Novel derivatives of prostaglandin compounds of the F-series (PGF), specifically macrocyclic internal 1,15-lactones of fluprostenol and related PGF analogs, such as cloprostenol or latanoprost. The novel analogs can be formulated into ophthalmic solutions and topically applied for the treatment of the increased intraocular pressure caused by glaucoma and the reduction of ocular hypertension.

3 Claims, 6 Drawing Sheets

STRUCTURE IV

FIG. 3A

CONTROL (PGF$_{2\alpha}$ METHYL ESTER) AND BOVINE CORNEA

TLC: 1 (2 HR)

LANE 1: PGF$_{2\alpha}$ METHYL ESTER (STANDARD)
LANE 2: PGF$_{2\alpha}$ METHYL ESTER AND BOVINE CORNEA
LANE 3: PGF$_{2\alpha}$ FREE ACID (STANDARD)

40:60:1 ACETONE/ DICHLOROMETHANE/ ACETIC ACID

LANE: 1 2 3

FIG. 3B

CONTROL (PGF$_{2\alpha}$ METHYL ESTER) AND BOVINE CORNEA

TLC: 2 (4 HR)

LANE 1: PGF$_{2\alpha}$ METHYL ESTER (STANDARD)
LANE 2: PGF$_{2\alpha}$ METHYL ESTER AND BOVINE CORNEA
LANE 3: PGF$_{2\alpha}$ FREE ACID (STANDARD)

40:60:1 ACETONE/ DICHLOROMETHANE/ ACETIC ACID

LANE: 1 2 3

FLUPROSTENOL 1,15-LACTONE AND BONVINE CORNEA
TLC: 1 (2 HR)

FLUPROSTENOL 1,15-LACTONE AND BONVINE CORNEA
TLC: 2 (4 HR)

Fluprostenol Lactone Experiment
Fluprostenol Lactone Control (#1) w/o cornea
Beckman C18; 250 x 4.6mm; 5U; SN 9UE877
222nm; p = 151 bar
70:30:0.1 MeOH: $H_2O$: HAc Fluprostenol Lactone Experiment
Cornea and Fluprostenol Lactone
Beckman C18; 250 x 4.6mm; 5U; SN 9UE877
222nm; p = 151 bar
70:30:0.1 MeOH: $H_2O$: HAc

INTERNAL 1,15-LACTONES OF FLUPROSTENOL AND RELATED PROSTAGLANDIN F2A ANALOGS AND THEIR USE IN THE TREATMENT OF GLAUCOMA AND INTRAOCULAR HYPERTENSION

CROSS-REFERENCE TO RELATED APPLICATION(S)

This is a continuation of U.S. patent application Ser. No. 09/776,574 filed on Feb. 1, 2001 now abandoned, which is a continuation of U.S. Ser. No. 60/179,508 filed on Feb. 1, 2000.

BACKGROUND OF THE INVENTION

The present invention relates to novel derivatives of prostaglandin compounds of the F-series (PGF), and more particularly to internal 1,15-lactones fluprostenol and related PGF analogs, and the use of such analogs for the treatment of increased intraocular pressure, such as that caused by glaucoma and the reduction of ocular hypertension.

The prostaglandins are a family of 20 carbon atom fatty acids, being structural derivatives of prostanoic acid, which exhibit useful activity in a wide variety of biological systems. Accordingly, prostaglandins represent useful pharmacological agents in the treatment and prevention of a wide variety of disease conditions. For a fuller discussion of prostaglandins and their uses, see Oates, et al., *New England J. Med.*, Vol. 319, No. 11, pp. 689-698 and Vol. 319, No. 12, pp. 761-768 (1988) and the references cited therein.

Prostaglandin $F_{2\alpha}$ ($PGF_{2\alpha}$) is a naturally-occurring prostaglandin which is widely manufactured and sold under a variety of trade names as an abortifacient, among other uses. See monograph 8065, page 1354 of *The Merck Index*, $12^{th}$ edition (1996). It is also well known in the art that naturally-occurring prostaglandins can be topically applied to lower intraocular pressure. However, naturally-occurring prostaglandins generally cause inflammation and surface irritation of the eye.

Analogs of $PGF_{2\alpha}$ which incorporate aromatic groups and other substituents into the omega chain have been prepared and found to be more potent and selective tetranor $PGF_{2\alpha}$, and its pharmacologic profile is described in monograph 4231, page 711 of *The Merck Index*, $12^{th}$ edition (1996). Unfortunately, the known synthetic analogs also produce the same undesirable side effects as the naturally-occurring compounds. There is, therefore, a need in the art for less inflammatory compounds for reducing intraocular pressure.

A number of simple $PGF_{2\alpha}$ analog esters have been found to be potent and selective agents useful for the treatment of ocular hypertension. For example, latanoprost is the isopropyl ester of 13,14-dihydro-17-phenyl-18,19,20-trinor $PGF_{2\alpha}$ and is widely marketed for the clinical treatment of glaucoma under the trade name Xalatan. See monograph 5387, page 918 of *The Merck Index*, $12^{th}$ edition (1996). Likewise, the isopropyl ester of fluprostenol and of similar $PGF_{2\alpha}$ analogs, such as cloprostenol, are specifically claimed as ocular antihypertensive agents in U.S. Pat. No. 5,665,773. The structures of naturally-occurring $PGF_{2\alpha}$ (Structure I), fluprostenol (Structure II), and latanoprost (Structure III) are shown hereinbelow. For a review of these agents, see Linden and Aim, *Drugs and Aging*, Vol. 14, No. 5, pp. 387-398 (1999).

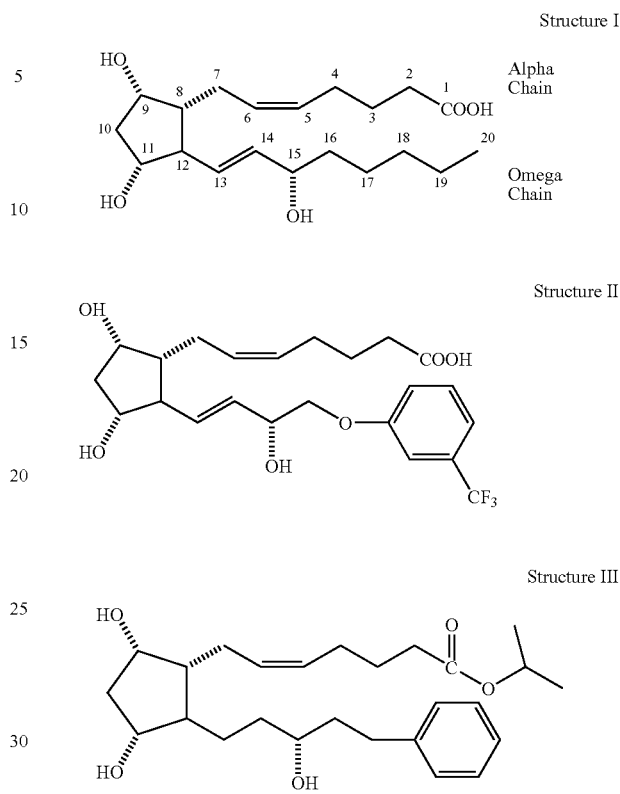

The esters of $PGF_{2\alpha}$ and its analogs are believed to act as prodrugs in the eye, in that the ester form which is administered is hydrolyzed by endogenous ocular esterase enzymes, releasing the PGF2α analog free acid as the active pharmacologic agent. However, this also releases a toxic and irritant small aliphatic alcohol such as isopropanol or methanol into the eye. This potential side effect of the prostaglandin esters was recognized by L. Z. Bito in one of the earliest inventions which specified the use of these esters in the eye (see, U.S. Pat. No. 4,599,353). This irritant side effect has also been recognized more recently in the form of iridial melanocyte hyperplasia and hyperpigmentation which has been documented in patients treated with ophthalmic solutions of isopropyl esters such as Unoprostone (See page 2 of NDA 21-214 for Rescula™ Ciba Vision.)

In addition to the foregoing, the isopropyl esters of $PGF_{2\alpha}$ analog compounds such as latanoprost and fluprostenol are highly viscous, glassy oils which are difficult to handle and to formulate into ophthalmic solutions. Worse yet, these compounds are prone to the retention of potentially toxic process solvents. There is, therefore, a need for a form of the prostaglandin analogs which is easier to handle and which does not release an irritant alcohol upon hydrolysis.

It is, therefore, an object of this invention to provide novel analogs of $PGF_{2\alpha}$ that are useful for the reduction of intraocular pressure with less inflammation and toxic side effects than the naturally-occurring compounds and known analogs.

It is another object of this invention to provide novel analogs of $PGF_{2\alpha}$ that preferably form orderly and high-melting crystals that can be easily handled and formulated into pharmaceutically-acceptable ophthalmic solutions.

It is also an object of this invention to provide novel ester analogs of $PGF_{2\alpha}$ that do not release toxic irritants into the eye upon hydrolysis.

SUMMARY OF THE INVENTION

The foregoing and other objects are achieved by this invention which provides, in a composition of matter aspect, novel macrocyclic internal 1,15-lactones of prostaglandins, and in particular internal 1,15-lactones of PGF2α analogs, such as the 16-aryloxy prostaglandin analogs, illustratively fluprostenol or cloprostenol.

We have discovered that it is possible to form an internal ester of $PGF_{2\alpha}$ analogs by creating a carbon-oxygen bond between the alcohol group at C-15 and the C-1 carboxylic acid. This creates a macrocyclic lactone that has novel and desirable characteristics. In fact, some of the novel analogs form highly crystalline structures that are easy to formulate into ophthalmic solutions, for example. The hydrolysis of these $PGF_{2\alpha}$ analog 1,15-lactones releases only the active $PGF_{2\alpha}$ analog free acid, without the production of a small aliphatic alcohol coproduct. Thus, these compounds are ideal and unique prodrugs for the treatment of glaucoma and other disorders causing an increase in intraocular pressure in the eyes of humans or animals.

For the purposes of this patent, the term "prostaglandin" is intended to mean any one of the prostanoic acid derivatives which include the ring type A, B, C, D, E, F, G, H, I, J and K, but most particularly those of the F-type. The term "derivative" is intended to mean all compounds which have a chemical affinity, resemblance, or structural character which clearly associates them with the prostanoids and in particular, prostanoic acid or $PGF_{2\alpha}$. The term "analog" is intended to mean any somewhat modified version of a natural product, in this case a prostaglandin, or a related synthetic analog, wherein a number of atoms such as carbon, hydrogen, oxygen or heteroatoms such as nitrogen, sulfur or halide have been added or deleted from the parent structure, so as to yield a new molecular compound.

The compounds of the present invention have the general Formula I:

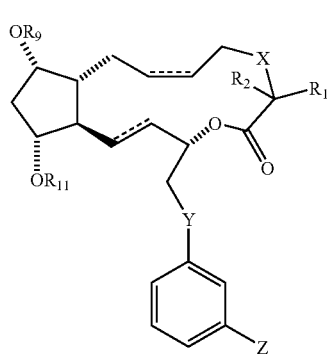

Formula I wherein X is O, S, NH or $CH_2$;

$R_1$ and $R_2$ are the same and are either H, $CH_3$ or F;

$R_9$ is H, or $C_1$-$C_{20}$ straight chain, saturated or unsaturated or branched acyl;

$R_{11}$ is H, or $C_1$-$C_{20}$ straight chain, saturated or unsaturated or branched acyl;

represents any combination of a single bond, or a cis or trans double bond;

Z is H, Cl, Br, I, $CF_3$, $CH_3$, or $C_1$-$C_{10}$ straight chain or branched alkyl;

Y is O, S, NH or $CH_2$.

In preferred embodiments the internal,15-lactone is an analog of the $PGF_{2\alpha}$, analog, fluprostenol. In particular, analogs of fluprostenol, having the structure of Formula I wherein $R_9$ and $K_{11}$ are H; Y is one of the polar substituents O, S, or NH; and Z is $CH_3$ are highly crystalline and therefore, are readily formulated into ophthalmic solutions for topical application.

In specific preferred embodiments of the present invention, the compound is the 1,15-lactone of fluprostenol (Structure IV), the 1-15-lactone of cloprostenol (Structure V), and the 1,15-lactone of latanoprost (Structure VI).

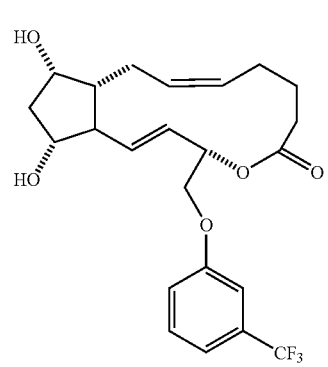

Structure IV

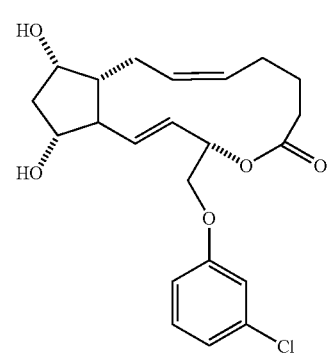

Structure V

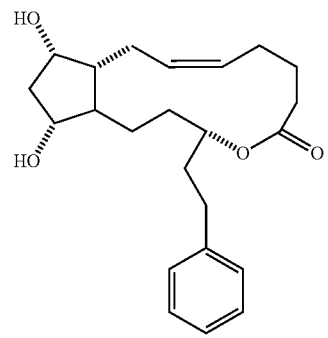

Structure VI

While the 1,15-lactones of $PGF_{2\alpha}$ analogs are the preferred embodiment of this invention, it is intuitively obvious that analogous 1,9 and 1,11-lactones of $PGF_{2\alpha}$ analogs would have some of the same advantages over the corresponding methyl or isopropyl esters, and thus these 9-and 11-membered-ring prostaglandin and prostaglandin analog cyclic lactones are specifically within the contemplation of the present invention.

The compounds of Formula I are active in lowering the intraocular pressure in humans and other animals and are therefore useful in the treatment of glaucoma and other disorders that cause an increase in intraocular pressure. Therefore, in a method of use aspect of the invention, a therapeutically effective amount of at least one compound having the structure of Formula I is administered to an affected eye to treat increased intraocular pressure. The preferred route of administration is via the topical application of sterile ophthalmic solutions directly into the eye.

In forming compositions for topical administration, the compounds of the present invention are generally formulated as between about 0.00003 to about 3 percent by weight (wt %) solutions in an aqueous solution buffered to a pH between 4.5 to 8.0 with a suitable buffering agent, and most preferably between 7.0-7.6. The compounds are preferably formulated as between about 0.0003 to about 0.3 wt % and, most preferably, between about 0.003 and about 0.03 wt %.

The dosage range for topical administration is between about 0.1 and 100 micrograms (μg) per eye per day, and is most preferably between 1 and 10 μg per eye per day. While the precise regimen is left to the discretion of the clinician, it is recommended that the resulting solution be topically applied by placing one drop in each eye one or two times a day.

A topical ophthalmic composition or formulation, in accordance with the present invention, broadly comprises a pharmaceutically acceptable carrier and a therapeutically effective amount of at least one compound having a chemical structure in accordance with Formula I.

In typical formulations, the carrier for the active agent(s) would be an aqueous solution buffered to physiologically-acceptable pH levels with an acidic or basic pH adjusting agent. Of course, the osmolarity of the solution would be adjusted with osmolarity adjusting agents, such as sodium chloride (NaCl) or potassium chloride (KCl), as is known in the art. Other ingredients which may be desirable to use in the ophthalmic preparations of the present invention include preservatives, co-solvents and viscosity building agents.

Ophthalmic products are typically packaged in multidose form, which generally require the addition of preservatives to prevent microbial contamination during use. Suitable preservatives include: benzalkonium chloride, thimerosal, chlorobutanol, methyl paraben, propyl paraben, phenylethyl alcohol, edetate disodium, sorbic acid, ONAMER M®, or other agents known to those skilled in the art. Such preservatives are typically employed at a concentration between about 0.001% and 1.0% by weight.

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; Tyloxapol®; Cremophor® EL; sodium dodecyl sulfate; glycerol; PEG 400; propylene glycol; cyclodextrins; or other agents known to those skilled in the art. Such co-solvents are typically employed at a concentration between about 0.01% and about 2% by weight.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a concentration between about 0.01% and about 2% by weight.

In a specific illustrative embodiment, a topical formulation for treating increased intraocular pressure, in accordance with the invention, comprises:

| Ingredient | Amount (by wt. %) |
|---|---|
| Fluprostenol 1,15-lactone | 0.002 |
| Dextran 70 | 0.1 |
| Hydroxypropyl methylcellulose | 0.3 |
| Sodium Chloride | 0.77 |
| Potassium Chloride | 0.12 |
| Disodium EDTA | 0.05 |
| Benzalkonium Chloride | 0.01 |
| HCl and/or NaOH | to pH = 7.0-7.6 |
| Purified water | q.s. to 100% |

BRIEF DESCRIPTION OF THE DRAWING

FIGS. 3A-3D are images of chromatography plates developed at 2 hours (FIGS. 3A and 3C) and 4 hours (FIGS. 3B and 3D), respectively, showing enzymatic hydrolysis of $PGF_{2\alpha}$ methyl ester and fluprostenol 1,15-lactone by corneal esterase enzymes.

DETAILED DESCRIPTION OF THE INVENTION

The compounds of the present invention can be synthesized from commercially available starting materials as described in the following examples. The synthetic procedures described in the following examples are representative in nature and are not intended to be limiting. In general, any of the compounds represented in Formula I may be prepared by analogous techniques and procedures known to persons of skill in the art.

EXAMPLE I

Synthesis of Fluprostenol 1,15-Lactone

Figure 1A:
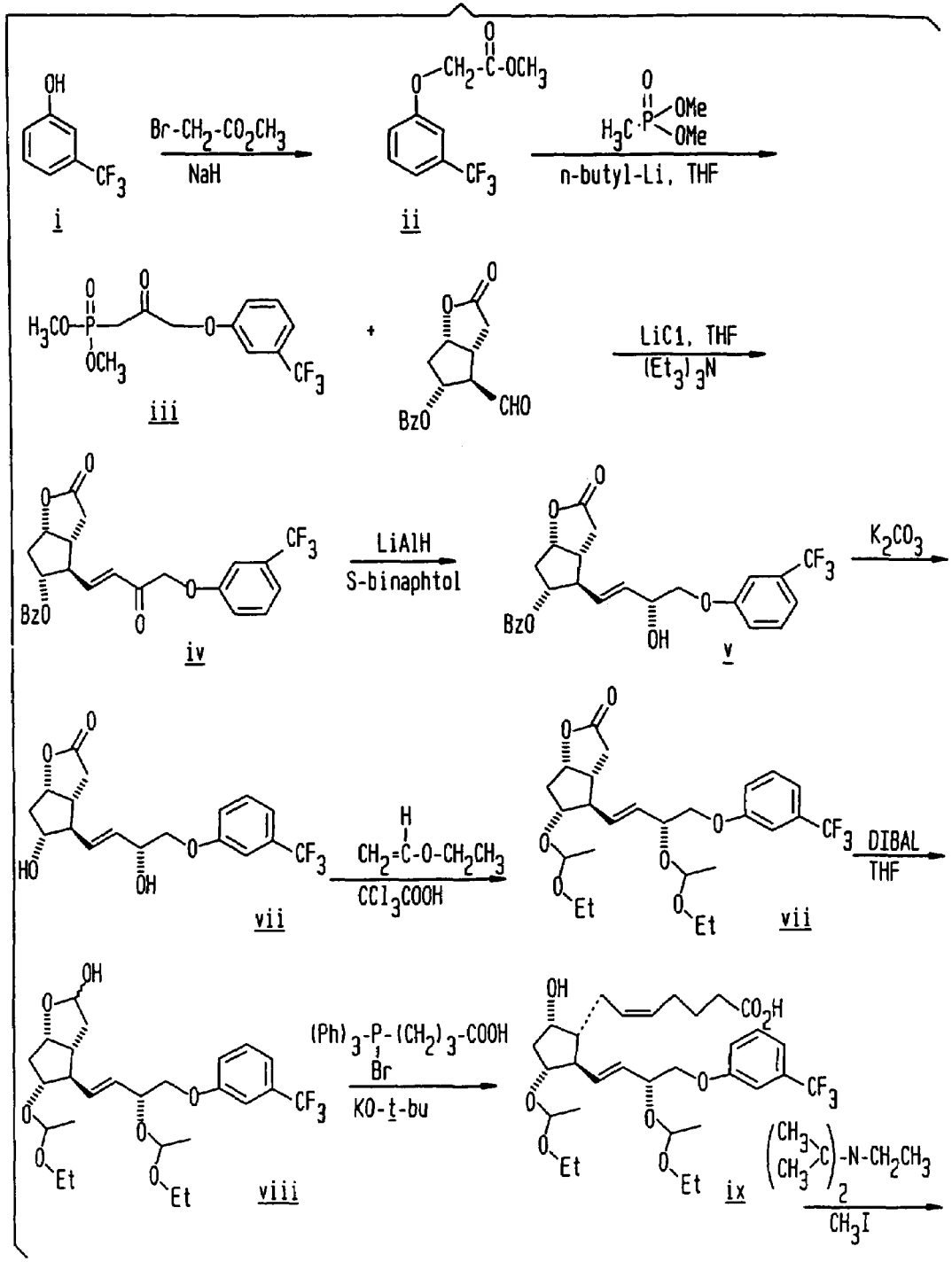
FIGS. 1A and 1B are illustrative synthetic schemes for producing fluprostenol 1,15-lactone.
Figure 1B:
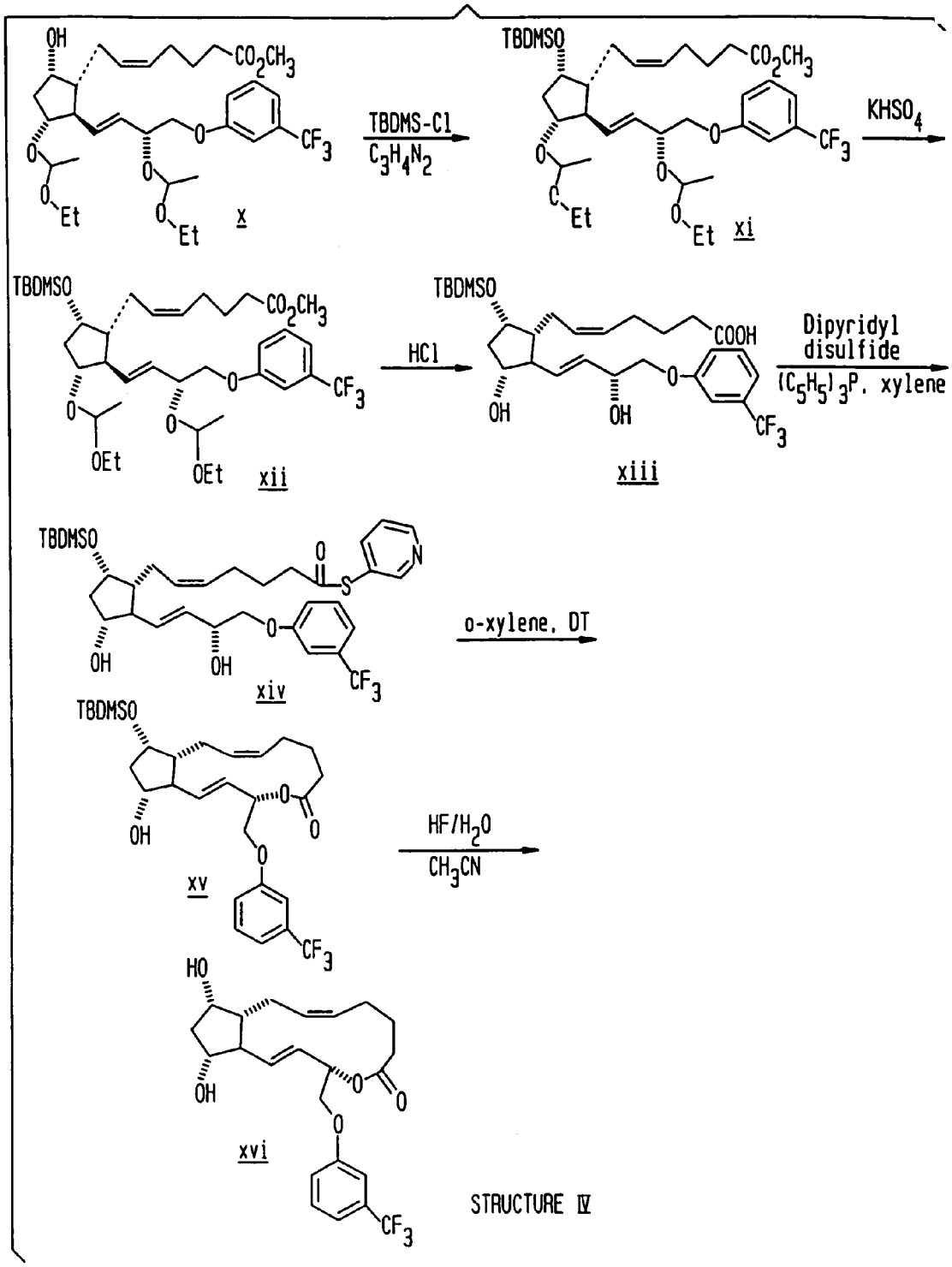

FIGS. 1A and 1B are illustrative synthetic schemes used to produce fluprostenol 1,15-lactone (Structure IV).

A 4 L, 3-neck round-bottom flask was dried in an oven at 110° C. overnight and fitted with an addition funnel, an overhead stirrer and a dry nitrogen gas inlet tube. Sodium hydride (NaH; 0.617 moles; 14.8 g) as a dry powder was suspended in 1.5 L of anhydrous tetrahydrofuran (THF). The mixture was cooled to 0° C. with an external ice bath and 75 ml (100 g; 0.617 moles) of m-trifluoromethyl cresol was added dropwise and stirred one hour at 0° C. and 2 hours at 22° C. The reaction mixture was then cooled to 0° C. and (47.3 ml; 0.5 moles) of methyl bromoacetate was added dropwise. The mixture was stirred an additional 2 hours at 0° C. and 1 hour at 22° C. 1.5 L of ethyl acetate was then added and the mixture transferred to a 6 L separatory funnel. 2 L of water was added and the layers were separated. The organic layer was washed twice with 1 L of brine, dried over solid anhydrous sodium sulfate, and the solvents evaporated to give 150 g of the trifluoromethyl compound ii as a yellow oil.

This product may be used directly in the next step of the synthesis, or more reliably may be purified by flash chromatography and used in a more purified form. The trifluoromethyl compound ii (86 g) is dissolved in 1.5 L of anhydrous THF and placed in a 2 L addition funnel over a 3-neck, 3 L round-bottom flask under dry nitrogen. Dimethyl methylphosphonate (63.3 ml) was added directly to the 3 L flask along with 1.2 L of anhydrous THF and cooled to −78° C. with an external dry ice/acetone bath while stirring well with a mechanical stirrer. 2.5 M n-butyl lithium (217.6 ml) was added dropwise. The mixture was stirred at −78° for 90 minutes, and the solution of compound ii was then added dropwise over 30 minutes. The reaction was maintained an additional 4 hours at −78° C. then stirred at ambient temperature overnight. The reaction mixture was then acidified with 2 L of 5% potassium hydrogen sulfate ($KHSO_4$) and transferred to a 6 L separatory funnel. It was diluted with 1.5 L of ethyl acetate, and the aqueous layer extracted once with 1 L of ethyl acetate and discarded. The organic layers were combined and washed with 1 L portions of brine until neutral, then dried over solid sodium sulfate and the solvent evaporated to give 237 g of yellow oil. This oil was purified by flash chromatography on silicic acid packed and eluted with 20:80 hexane:ethyl acetate. Pure fractions were combined and evaporated to give 175 g of the phosphonate compound iii.

The phosphonate compound iii (175.2 g; 537 mmol), Corey aldehyde (122.6 g; 447 mmol), and lithium chloride (22.8 g; 537 mmol) were placed in a 5 L round-bottom flask fitted with a dropping funnel under an atmosphere of nitrogen. Using a double-ended needle 3 L of anhydrous THF was added to the flask. The reaction mixture was cooled externally to −4 to −10° C. using ice and sodium chloride. To this reaction mixture triethyl amine (75 ml; 537 mmol) was added dropwise over a period of 3 hours. The reaction mixture was allowed to warm to room temperature and stirred overnight at ambient temperature. The reaction mixture was diluted by the addition of 1 L of ethyl acetate and 1 L of water. The pH of the reaction mixture was brought to neutral by the addition of 5% potassium hydrogen sulfate. The reaction mixture was transferred to a 6 L separatory funnel. The organic phase was separated from the aqueous phase. The aqueous phase was extracted with 500 ml of ethyl acetate and then discarded. The combined organic extracts were washed with 200 ml of brine and dried over sodium sulfate. Removal of solvent on a rotary evaporator under reduced pressure afforded 250 g of the oil. The oil was purified on a silica gel column using 40:60 ethyl acetate:hexane as the eluant to afford 145 g of the enone compound iv.

In a 3 L, 3-neck round-bottom flask, 210 ml of ethanol (2 M solution in THF) were added dropwise to 420 ml of lithium aluminum hydride (1 M solution in THF) under an atmosphere of nitrogen. Next 120 g (420 mmol) of (S)-binaphtol dissolved in 300 ml of THF were added dropwise to the reaction mixture. The reaction mixture was stirred at ambient temperature for a period of one hour. The reaction mixture was then cooled externally to −100° C. in a dry-ice ether bath. This was followed by the dropwise addition of the enone compound iv (100 g; 210 mmol) in 300 ml of THF. The reaction mixture was stirred at −100° C. for 4 hours and at −78° C. for 48 hours. To the reaction mixture 200 ml of methanol were added at −78° C. and the reaction mixture was allowed to warm to room temperature. The reaction mixture was then acidified to pH 6 with 5% potassium hydrogen sulfate. The reaction mixture was then diluted with 1500 ml of ethyl acetate and 1500 ml of water. The organic phase was separated from the aqueous phase. The aqueous was extracted with 750 ml of ethyl acetate and discarded. The combined organic phases were washed with 1000 ml of brine and dried over sodium sulfate. Removal of solvent on a rotary evaporator under reduced pressure afforded 200 g of an oil. The oil was purified on a silica gel column using 10:90 acetone:hexane as the eluant to afford 60 g of the benzoate alcohol compound v.

A solution of the benzoate alcohol compound v (60 g; 126 mmol) in 900 ml of methanol was placed in a 2 L round-bottom flask. Potassium carbonate ($K_2CO_3$; 21 g; 159 mmol) was added and the reaction mixture was stirred at ambient temperature for 90 minutes. The reaction mixture was cooled to 0° C. and acidified to pH 6 with 5% potassium hydrogen sulfate. The reaction mixture was diluted with 1500 ml of brine and extracted twice with 1 L of ethyl acetate. The organic layers were combined and washed with brine until it had a neutral pH. The organic phase was dried over sodium sulfate and concentrated on a rotary evaporator under reduced pressure to afford an oil which was purified on a silica gel column using 90:10 ethyl acetate:hexane as the eluant to furnish the desired lactone diol compound vi.

A 3 L jacketed-flask was equipped with a mechanical stirrer and a temperature microprocessor. The flask was charged with the lactone diol compound vi (~148 g; 0.397 moles) and approximately 2000 ml of methylene chloride under an atmosphere of nitrogen. This mixture was stirred until dissolved.

Approximately 7 equivalents of ethyl vinyl ether (266 ml; 2.779 moles) was added to the flask followed by the addition of approximately 0.1 equivalents of trichloroacetic acid (6.49 g; 0.0397 moles). The reaction mixture was stirred at room temperature until the reaction was judged to be complete by monitoring the reaction progress with thin layer chromatography (TLC). In this case, the reaction mixture was spotted on a silica gel TLC plate alongside a spot of the starting material. The spotted plate was placed into a TLC tank containing 80% ethyl acetate, 20% hexane (v/v). To develop, the TLC plate was sprayed with a 50:50 mixture of sulfuric acid and water (v/v) and heated. In some instances, it may be necessary to heat the reaction mixture to 30° C.±5° for the reaction to go to completion.

While the reaction mixture is going to completion, a 10% potassium bicarbonate solution was prepared by combining approximately 10 g of potassium bicarbonate with approximately 250 ml of tap water in a 250 ml Erlenmeyer flask and swirling until dissolved. A 28% solution of sodium chloride was also be prepared by combining approximately 140 g of sodium chloride with approximately 500 ml of tap water in a 1 L Erlenmeyer flask and swirling until dissolved.

When the reaction was judged to be complete, approximately 100 ml of the 10% potassium bicarbonate solution was added to the reaction mixture and stirred for about 20 minutes. The reaction mixture was poured into a 6 L separatory funnel. The 3 L jacketed-flask, used as a reaction vessel, was washed with about 200 ml methylene chloride and added to the separatory funnel. The separatory funnel was agitated to mix the phases and the bottom organic layer was drawn off into a 4 L flask. The remaining aqueous potassium bicarbonate layer was washed with approximately 200 ml of methylene chloride. The organic phase was collected and the aqueous phase discarded.

The collected organic phase was washed with approximately 200 ml of tap $H_2O$ in a separatory funnel, and the aqueous phase discarded. The organic phase was washed again with approximately 500 ml of the 28% sodium chloride solution. The aqueous phase was discarded and the the collected organic phase was placed in a 4 L flask and dried by adding approximately 100 g sodium sulfate and waiting about 30 minutes.

The dried organic phase was decanted off the sodium sulfate into a 4 L flask. The sodium sulfate was washed with approximately 700 ml of methylene chloride, decanted and combined with the organic solution. The solvent was evaporated from the dried, collected reaction mixture in vacuo on a rotary evaporator, in portions, using a 2 L round-bottom flask until the reaction mixture was reduced to a viscous oil, the diethoxyethyl ether compound vii.

The di-protected, diethoxyethyl ether compound vii was dissolved in, and washed from, the 2 L round-bottom flask with approximately 2300 ml of toluene, and poured into a 6 L jacketed-vessel. Using a double-ended needle, approximately 1.5 equivalents of diisobutyl aluminum hydride (DIBAL) in toluene (1.5 M solution) was transferred slowly, over a 30 to 60 minute time period, to an addition funnel attached to the 6 L reaction vessel while maintaining a stirring solution temperature of $-70°$ C.$\pm 10°$ C. The reaction mixture was stirred for about 2.5 hours at $-70°$ C.$\pm 10°$ C. while being monitored for completion by TLC. To monitor for completeness, the reaction mixture was spotted on a silica gel TLC plate alongside a spot of the starting material. The spotted plate was placed into a TLC tank containing 50% ethyl acetate, 50% hexane (v/v). To develop, the TLC plate was sprayed with a 50:50 mixture of sulfuric acid and water (v/v) and charred with heat. Once the reaction was judged to be complete, the heating circulator was turned off.

Approximately 0.31 equivalents of tap water (to DIBAL) and approximately 700 ml THF was combined in a 1 L Erlenmeyer flask and chilled. Excess DIBAL was decomposed by adding the chilled mixture of water and THF to the stirring solution through the addition funnel attached to the 6 L reaction vessel. The water/THF solution should be added dropwise and slowly. In particular, the first 50-100 ml should be added very slowly because foaming can occur. The temperature was allowed to rise during the addition. Once the addition is complete, the temperature should be between 0° C. to $-45°$ C.

Using the Fisher circulator, the reaction was warmed to approximately 20° C. and then stirred for about 1 hour. A temperature of about 28° C.$\pm 10°$ C. should be maintained. After about 30 minutes, the reaction tends to heat up because the salts are hydrating. Over the 1 hour period, the reaction mixture went from a dull yellowish-brown color to a titanium white slurry.

Approximately 990 ml toluene and approximately 660 ml THF was combined in a separate flask. Approximately 2 inches of celite 545 was placed in a 2 L fritted-funnel and enough of the mixture was poured over the top of the celite so that it was totally covered. Once the reaction was complete, the slurry was filtered over the celite using a water aspirator for suction. A stream of nitrogen was aimed at the filter funnel during filtration. The filter cake and reaction vessel was washed with the toluene/THF. The filter cake was discarded. The solvent was evaporated to give lactol compound viii as a viscous yellow oil which was used directly, without purification in the next step.

4-Carboxybutyl triphenylphosphine bromide (8.57 g; 19.34) was suspended in 30 ml of THF (anhydrous). Potassium tert-butoxide (38.68 ml; 38.68 mmol) was slowly added to this suspension. The reaction mixture was stirred at room temperature for 45 minutes and then cooled down to $-10°$ C. with ice/NaCl. Subsequently, lactol compound viii, dissolved in 20 ml of anhydrous THF, was added drop by drop to the reaction mixture. The resulting reaction mixture was stirred at $-10°$ C. for 2 hours, and then brought up to room temperature, acidified with 5% $KHSO_4$, and diluted with 200 ml of brine. The mixture was then extracted 2 times with 200 ml of ethyl acetate. The organic extract was washed twice with 200 ml of brine, dried over sodium sulfate, filtered, and evaporated. The mixture was purified on acid-washed silica gel using 40:60 acetone/hexane to flush the column. Mass of collected product, 11,15-di-(2-ethoxyethyl)-fluprostenol, compound ix, was 5.75 g (98.0% yield).

Compound ix (5.75 g; 9.48 mmol) was dissolved in 40 ml of anhydrous acetonitrile. N,N-diisopropylethylamine (3.8 g; 5.12 ml; 29.44 mmol) and iodomethane (4.04 g; 1.77 ml; 28.44 mmol) were added to this solution. The reaction mixture was stirred at 0° C. for 30 minutes, then at room temperature overnight. The reaction mixture was diluted with 200 ml of ethyl acetate and washed with 200 ml of water and then 200 ml of brine. The organic extract was dried over sodium sulfate, filtered, and evaporated. The oily residue was purified on a normal silica gel column using 40:60 ethyl acetate/hexane to flush the column. Mass of collected product, 11,15-di-(2-ethoxyethyl)-fluprostenol methyl ester, compound x, was 5.55 g (94.89% yield).

Compound x (5.58 g; 8.99 mmol) was dissolved in 50 ml of dimethylformamide (DMF). tert-Butyl-dimethylsilyl chloride (TBDMS chloride; 5.39 g) and imidazole (2.68 g) were added to this solution. The reaction mixture was stirred at room temperature overnight, and then taken up in 200 ml of ethyl acetate, washed with 50 ml of brine, dried over sodium sulfate, and evaporated. The oily residue was purified on a normal silica gel column using 10:90 ethyl acetate/hexane to flush the column. Mass of collected product, 9-TBDMS-11,15-di-(2-ethoxyethyl)-fluprostenol methyl ester, compound xi, was 5.99 g (94.65% yield).

Compound xi (5.99 g; 8.67 mmol) was dissolved in 40 ml of methanol and 26 ml (26 mmol) of 1 M sodium hydroxide was added drop by drop. The reaction mixture was stirred at room temperature overnight. The reaction mixture was then acidified with 5% $KHSO_4$ diluted with 200 ml of brine and extracted twice with 100 ml of ethyl acetate. The organic extract was washed twice with 100 ml of brine, dried over sodium sulfate and evaporated. The residue was purified on an acid-washed silica gel column using 10:90 ethyl acetate/hexane as eluent. Mass of collected product, 9-TBDMS-fluprostenol 11,15-diethoxyethyl ether, compound xii, was 5.64 (95.40% yield).

Compound xii (3 g) was dissolved in 100 ml of THF in a 500 ml round-bottom flask and stirred, under a nitrogen atmosphere, at room temperature. Following the addition of 0.5 M hydrochloric acid (2.0 ml), the reaction mixture was stirred at ambient temperature for 2 hours. The reaction mixture was then diluted with ethyl acetate, saturated with brine, and extracted once with ethyl acetate. The combined organic solvents were dried over anhydrous sodium sulfate and the solvents were removed under reduced pressure to give 2.57 grams of fluprostenol 9-TBDMS ether, compound xiii, as a viscous oil.

Compound xiii (2.57 g; 5.9 mmol) was dissolved in 30 ml of anhydrous (oxygen free) xylene. To this solution, 2,2'-dipyridyl bisulfide (1.59 g; 7.2 mmol) and triphenylphosphine (1.89 g; 7.2 mmol) was added. The reaction mixture was stirred at room temperature under a nitrogen atmosphere for 24 hours. Reaction progress was checked via TLC plates developed in 40:60 acetone/hexane, as described hereinabove. The resulting product was crude thiopyridyl ester 9-TBDMS fluprostenol, compound xiv.

Anhydrous o-xylene (180 ml) was brought to reflux in a 1000 ml round-bottom flask under a nitrogen atmosphere. The crude compound xiv solution was added slowly to the refluxing xylene. The mixture was then refluxed for 3 hours under a nitrogen atmosphere. The reaction mixture was allowed to cool to room temperature and was stirred for 24 hours. The reaction progress was check with TLC plates developed in 40:60:1 acetone/hexane/acetic acid. The resulting crude lactone mixture was evaporated to give a viscous oil which was purified by chromatography on silica gel (300 g) packed and eluted with 1:4 acetone:dichloromethane.

Fractions containing the desired 9-TBDMS fluprostenol 1,15-lactone, compound xv, were combined and evaporated to give 370 mg of the desired compound as a colorless, viscous oil. The oil was transferred to a 50 ml round-bottom flask. A 5:95 mixture of 40% hydrofluoric acid (HF) in acetonitrile (10 ml) was added to the oil and the mixture stirred at ambient temperature for 5 hours. The mixture was then diluted with 100 ml of ethyl acetate and washed 3 times with 100 ml portions of brine. The organic phase was dried over anhydrous sodium sulfate and evaporated to give crude fluprostenol 1,15-lactone, compound xvi, as a viscous film. The crude lactone was purified on silicic acid packed and eluted with 15:85 acetone:dichloromethane. Pure fractions were combined and evaporated to give a semisolid mass. This mass was recrystallized from diethyl ether/hexane to give 125 mg of fine white crystals of compound xvi (Structure IV) which melted sharply at 127-128° C. The IR spectrum showed strong absorbance bands at 3452 (OH); 2933 (CH); 1708 (C=O); 1653 and 1617 (C=C, E and Z) with additional bands at 1559; 1498; 1451; 1332 (C—F); 1240; 1168; 1126; 1042; 979; 870; and 795 cm$^{-1}$.

The mass spectrum of compound xvi was run on a Finnegan LCQ mass spectrometer in API mode gave a base peak of 26 1.1 amu corresponding to the molecular ion (440 amu) minus 1120 (18) minus trifluoromethyl eresole (161). Also observed was a strong peak at 279. 1 amu corresponding to the molecular ion after loss of trifluoromethyl cresol. The molecular ion itself was not observed; when infused into the instrument as a solution in methanol, an ion at 472 amu, consistent with methanolys is of the lactone, was observed. Likewise, when infused as a solution in ethanol, the higher molecular weight ion of the ethyl ester at 486 amu was observed.

The proton nmr in CDCl$_3$ showed: complex multiplet at 7.0-7.4 ppm (4H); complex multiplet 5.8-6. 1 ppm (2 K); unresolved multiplet 5.5-5.7 ppm (2 K); unresolved multiplet 5.3-5.5 ppm (IH); unresolved multiplet 4.0-4.3 ppm (4H); unresolved multiplet 1.1-2.5 ppm (not integrable; at least 12 K).

The TLC analysis of fluprostenol 1,15-lactone on normal phase, Silica gel G-60 plates eluted in 40:60 acetone: dichloromethane gave a single spot at Rf=0.5; the Rf of a co-spotted standard of fluprostenol in this system is 0.0. When 0.5% acetic acid was added to the development solvent, the Rf of the fluprostenol 1,15-lactone was unchanged, while that of fluprostenol increased to 0.16. A 2 mg sample of fluprostenol 1,15-lactone dissolved in 2 ml of methanol and treated with 2 ml of 1M NaOH was converted over a 2 hour period to a more polar product which co-migrated with the fluprostenol standard in 40:60 acetone: dichloromethane containing 0.5% acetic acid.

EXAMPLE 2

Synthesis of Latanoprost 1,5-Lactone

Figure 2:
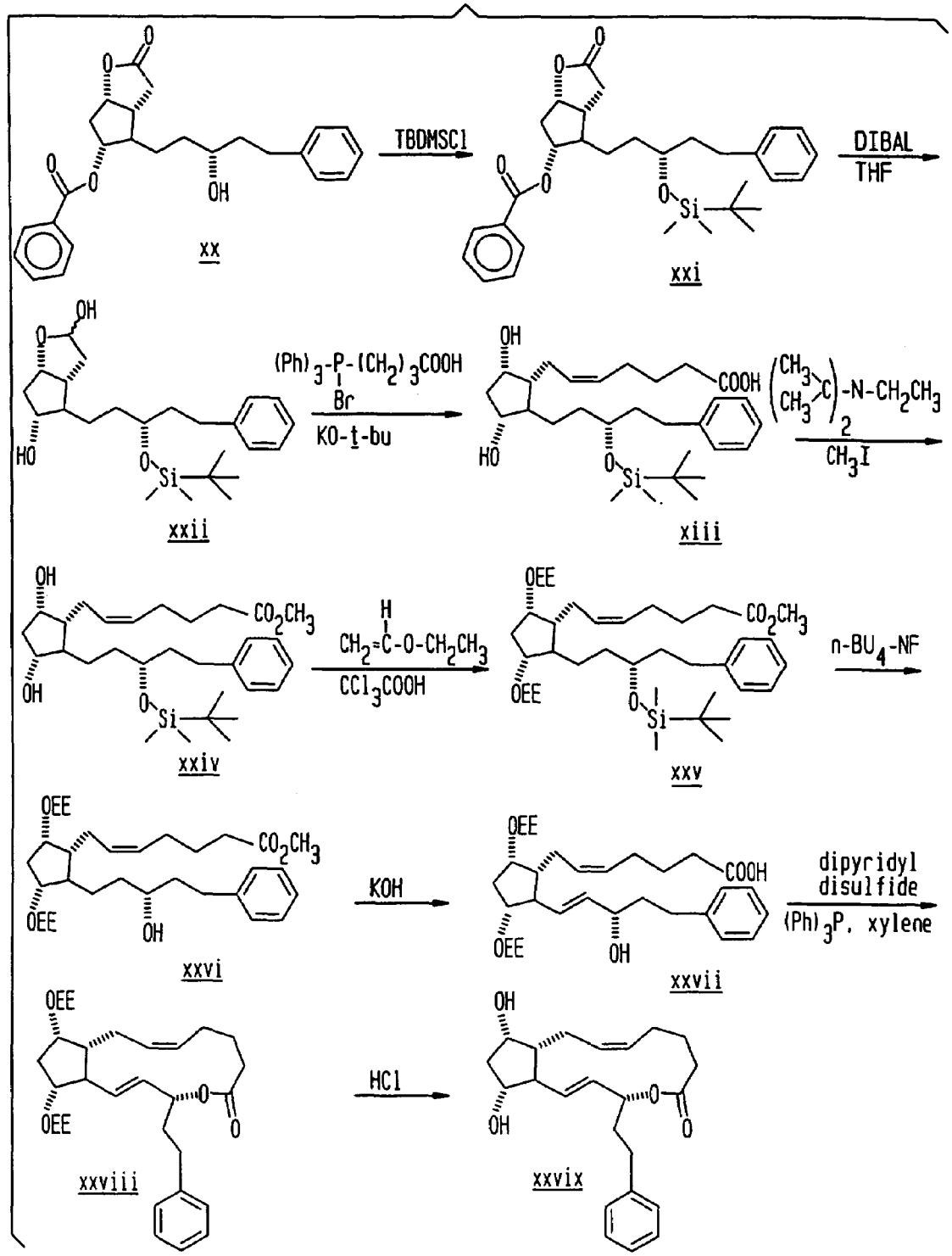
FIG. 2 is an illustrative synthetic scheme for producing latanoprost 1,15-lactone.

FIG. 2 is an illustrative synthetic scheme used to prepare the 1,1 5-lactone of 17-phenyl-20,19,18-trinor PGF$_{2\alpha}$, or latanoprost 1,15-lactone (Structure VI).

The starting compound is a commercially available benzoate lactone diol, compound xx (See Cayman Chemical Catalog No. 70039). Compound xx, or 13,14-dihydro-15 (R)-hydroxy-17-phenyl PG lactone 11-benzoate (6.0 g; 14.69 mmol) was dissolved in 60 ml of DMF (anhydrous) in a dry 500 ml round-bottom flask. Imidazole (3.03 g; 44.07 mmol) and TBDMS chloride (6.64 g, 44.07 mmol) was added slowly with stirring under a nitrogen atmosphere. The reaction mixture was stirred at room temperature overnight. The reaction mixture was then diluted with 200 ml of water and extracted with 300 ml of ethyl acetate acidified with 5% potassium hydrogen sulfate, and washed with 200 ml of brine. The combined aqueous mixture was then extracted 2× with 200 ml of ethyl acetate. The organic extract was washed twice with 200 ml of brine, dried over anhydrous sodium-sulfate, filtered, and evaporated. The mixture was purified on 500 g of flash chromatography silica gel packed and eluted with 15:85 ethyl acetate/hexane. The product, mono-protected 15-TBDMS ether compound xxi, was a clear, colorless viscous oil. Mass of collected product was 7.42 g (96.6% yield).

Compound xxi showed a single spot at Rf=0.20 on silica gel-G TLC plates developed in 15:85 ethyl acetate/hexane and visualized with sulfuric acid/charring. An nmr scan (300 MHz-Bruker) run on compound xxi dissolved in deuterochloroform revealed a doublet at 8.05 ppm (2H); multiplet at 7.6 ppm (1H); triplet at 7.5 ppm (2H); multiplet at 7.2-7.4 ppm (5H); a pair of multiplets at 5.1-5.2 ppm (2H); a multiplet at 3.7 ppm (1H); broad multiplets from 2.3-3.0 ppm (8H); broad multiplets from 1.3-1.8 ppm (7H); single sharp singlet at 0.9 ppm (9H) and another sharp singlet at 0.02 ppm (6H), the latter two being the dimethyl silyl and the t-butyl methyl silyl groups, respectively.

Compound xxi (7.42 g; 9.48 mmol) was dissolved in 50 ml of anhydrous toluene in a 500 ml round-bottom flask equipped with a magnetic stirrer and fitted with a nitrogen inlet and an addition funnel. The flask was cooled to −78° C., and 57 ml of a 1.0 M solution of DIBAL was added dropwise over 20 minutes. The mixture was maintained at −78° C. and stirred for 2 hours. Then, 42 ml of water and 84 ml of THF were added, dropwise, through the addition funnel over 30 minutes. The reaction was allowed to warm to room temperature with vigorous stirring for 2 hours. The reaction solution was then filtered through a pad of celite, and the solids were rinsed with toluene. The solvents were evaporated from the filtrate to give a clear, viscous oil, a lactol compound xxii.

Compound xxii was dissolved in 30 ml of anhydrous THF and placed in an addition funnel. 4-Carboxybutyl triphenylphosphonium bromide (15.6 g; 35.5 mmol) was combined with 40 ml of anhydrous THF in a dry, 1000 ml round-bottom flask equipped with a nitrogen inlet, stir bar and the addition funnel containing the compound xxii. 1.0 M potassium t-butoxide in THF (71 ml) was added via syringe directly to the stirred slurry of the triphenylphosphonium bromide at room temperature and allowed to react for one hour. The reaction mixture turned dark orange. The reaction mixture was then cooled to 0° C. and the contents of the addition funnel added dropwise over 15 minutes, and the reaction mixture was stirred for an additional 18 hours. The solution was then diluted with 250 ml of water, 250 ml of ethyl acetate, and saturated potassium hydrogen sulfate until the pH was less than 3. The mixture was extracted three times with 200 ml of ethyl acetate. The combined organic extracts were washed with saturated brine, dried over anhydrous sodium sulfate, and evaporated to give a crude yellow oil which was chromatographed on 500 g of acid-washed (pH<6.2) silica gel packed and eluted with 15% acetone in dichloromethane. The product-containing fractions were combined and the solvent evaporated to give 6.0 g (85% yield) of 13,14-dihydro-17-phenyl, 20,19,18-trinor prostaglandin $F_{2\alpha}$, 15-TBDMS ether compound xxiii.

Compound xxiii, also designated as latanoprost free acid, 15-TBDMS ether, has an Rf of 0.25 on silica gel GF TLC plates eluted in 15:85:1 acetone:dichloromethane:acetic acid and visualized with sulfuric acid/charring.

Compound xxiii was dissolved in deutero-chloroform and an nmr (300 MHz-Bruker) was run, revealing a multiplet at 7.2-7.25 ppm (SH); a broad multiplet at 5.4 ppm (2H); three poorly defined multiplets at 3.7, 3.9 and 4.1 ppm (3H) superimposed on a poorly defined broad absorbance spanning this entire area (1H); broad multiplets from 1.3-2.8 ppm (31H); single sharp singlet at 0.9 ppm (9H) and another sharp singlet at 0.02 ppm (6H), the latter two being the dimethyl silyl and the t-butyl methyl silyl groups, respectively.

A solution of compound xxiii (6.0 g; 11.9 mmol) in 50 ml of anhydrous acetonitrile was placed in a 500 ml round-bottom flask and stirred at room temperature under a nitrogen atmosphere. The solution was cooled to 0° C. and diisopropylethyl amine (6.2 ml; 35.7 mmol) was added, followed by 2.2 ml of iodomethane (35.7 mmol). The reaction mixture was stirred one hour at 0° C., and then 12 hours at room temperature. The mixture was then diluted with ethyl acetate, washed with water (200 ml) and then brine (200 ml×3) and dried over anhydrous solid sodium sulfate. The solvent was evaporated under reduced pressure, and the crude product chromatographed over a 15×5 cm silica gel column packed and eluted with 40:60 ethyl acetate/hexane. Pure fractions were combined to give 5.5 g of the latanoprost methyl ester, 15-TBDMS ether compound xxiv.

Compound xxiv has an Rf of 0.35 on silica gel GF TLC plates eluted in 40:60 ethyl acetate:hexane and visualized with sulfuric acid/charring. Compound xxiv was dissolved in deutero-chloroform and an nmr (300 MHz-Bruker) was run, revealing a multiplet at 7.2-7.25 ppm (5H); a broad multiplet at 5.4 ppm (2H; three poorly defined multiplets at 3.7, 3.9 and 4.1 ppm (3H) a sharp singlet at 3.65 ppm (3H); broad multiplets from 1.3-2.8 ppm (31H); single sharp singlet at 0.9 ppm (9H) and another sharp singlet at 0.02 ppm (6H), the latter two being the dimethyl silyl and the t-butyl methyl silyl groups, respectively.

A solution of compound xxiv (4.5 g; 8.7 mmol) in 100 ml of anhydrous dichloromethane was stirred at room temperature in a 250 ml round-bottom flask under a nitrogen atmosphere. Ethyl vinyl ether (8.3 ml; 10 equiv.) was added to the flask along with a catalytic amount (142 mg) of trichloroacetic acid. The reaction mixture was stirred at room temperature for 3 days. Then the mixture was poured into brine and extracted with ethyl acetate. The extracts were washed three times with brine, then dried over solid sodium sulfate and the solvent evaporated under reduced pressure. The crude di-protected, di-ethoxyethyl ether compound was chromatographed on an 95×5 cm silica gel column packed and eluted with 10:90 ethyl acetate/hexane and the pure fractions of the di-protected compound xxv (1.6 g) were separated from the mono-protected compound (2.9 g)

The pure di-protected compound xxv, 9,11-di-ethoxyethyl ether, 15-TBDMS ether latanoprost methyl ester, has an Rf of 0.35 on silica gel GF TLC plates eluted in 15:85 ethyl acetate/hexane and visualized with sulfuric acid/charring. Compound xxv was dissolved in deutero-chloroform and an nmr (300 MHz-Bruker) was run, revealing a multiplet at 7.2-7.25 ppm (5H); a broad multiplet at 5.4 ppm (2H); a multiplet at 4.7 ppm (2H) representing the acetal methyne proton; three poorly defined multiplets at 3.7, 3.9 and 4.1 ppm (3H) superimposed on a poorly defined broad absorbance spanning this entire area (1H); a sharp singlet at 3.65 ppm (3H) and a multiplet at 3.5-3.6 ppm (4H); broad multiplets from 1.3-2.8 ppm (31H); single sharp singlet at 0.9 ppm (9H) and another sharp singlet at 0.02 ppm (6H), the latter two being the dimethyt silyl and the t-butyl methyl silyl groups, respectively.

A solution of compound xxv (1.3 g) in 25 ml of anhydrous THF was stirred at room temperature under a nitrogen atmosphere in a 200 ml round-bottom flask. A 1.0 M solution of tetra-n-butyl ammonium fluoride in THF (25 ml) was added, and the mixture was allowed to stir at room temperature overnight. The mixture was then acidified with 5% potassium hydrogen sulfate, extracted with ethyl acetate, and the combined extracts were rinsed with 100 ml of brine, then dried over solid sodium sulfate. The volatile solvents were evaporated under reduced pressure, and the crude product was purified on a 30×1.5 cm silica gel column packed and eluted in 30:70 ethyl acetate/hexane. Pure fractions were combined to give 350 mg of pure compound xxvi, 9,11-di-ethoxyethyl ether latanoprost methyl ester.

Compound xxvi has an Rf of 0.26 on silica gel GF TLC plates eluted in 30:70 ethyl acetate/hexane and visualized with sulfuric acid/charring. The product was dissolved in deutero-chloroform and an nmr (300 MHz-Bruker) was run, revealing a multiplet at 7.2-7.25 ppm (5H); a broad multiplet at 5.4 ppm (2H); a multiplet at 4.7 ppm (2H) representing the acetal methyne proton; three poorly defined multiplets at 3.7, 3.9 and 4.1 ppm (3H) superimposed on a poorly defined broad absorbance spanning this entire area (1H); a sharp singlet at 3.65 ppm (3H) and a multiplet at 3.5-3.6 ppm (4H); broad multiplets from 1.3-2.8 ppm (31H); peaks representative of the TBDMS group were notably absent.

A solution of compound xxvi (350 mg) in 5 ml of methanol and 1.5 ml THF was stirred at room temperature in a 100 ml pear-shaped flask. A 1 M solution of potassium hydroxide in water (1.5 ml) was added, and the mixture stirred at room temperature overnight. The reaction was then quenched with 10 ml of 5% potassium hydrogen sulfate. The mixture was extracted with ethyl acetate and the organic extract was rinsed with 50 ml brine followed by drying over solid anhydrous sodium sulfate. The volatile solvents were evaporated under reduced pressure, and the crude product was purified on a 72×2 cm silica gel column packed with acid-washed (pH=5.0) silica gel packed and eluted with 30:70 ethyl acetate/hexane. The pure fractions were combined to give 320 mg of the pure di-protected acid, 9,1 L-diethoxyethyl ether latanoprost free acid, compound xxvii.

Compound xxvii has an Rf of 0.27 on silica gel GF TLC plates eluted in 30:70:1 ethyl acetate/hexane/acetic acid and visualized with sulfuric acid/charring. Compound xxvii was dissolved in deutero-chloroform and an nmr (300 MHz-Bruker) was run, revealing a multiplet at 7.2-7.25 ppm (5H); a broad multiplet at 5.4 ppm (2H); a multiplet at 4.7 ppm (2H) representing the acetal methyne proton; three poorly defined multiplets at 3.7, 3.9 and 4.1 ppm (3H) superimposed on a poorly defined broad absorbance spanning this entire area (1H); a multiplet at 3.5-3.6 ppm (4H); broad multiplets from 1.3-2.8 ppm (31H).

A solution of compound xxvii (200 mg) in 5 ml of anhydrous xylene was stirred at room temperature in a 250 ml round-bottom flask under a nitrogen atmosphere. Triphenylphosphine (147 mg) and 108 mg of 2,2'-dipiridyl disulfide were added to the solution and the resulting mixture was stirred at room temperature for 18 hours. The mixture was then diluted with 50 ml of anhydrous xylene and refluxed for 3 hours, cooled to room temperature and stirred overnight. The solvent was evaporated under high vacuum and the residual oil was chromatographed on a 62×1.5 cm silica gel column packed with pH 5.0 silicic acid and eluted with 10:90 acetone/hexane. Pure fractions were combined and evaporated to give 89 mg of pure compound xxviii, 9,11-diethoxyethyl latanoprost 1,15-lactone.

Compound xxviii had an Rf of 0.57 on silica gel GF TLC plates eluted in 20:80 acetone/hexane and visualized with sulfuric acid/charring. Compound xxviii was dissolved in deutero-chloroform and an nmr (300 MHz-Bruker) was run, revealing a multiplet at 7.2-7.25 ppm (5H); a broad multiplet at 5.5 ppm (2H); a multiplet from 5.3-5.4 ppm and 5.2 ppm (1H); a multiplet at 4.7 ppm (2H) representing the acetal methyne proton; three poorly defined multiplets at 3.7, 3.9 and 4.1 ppm (1H) and a poorly defined multiplet from 3.4-3.8 ppm (4H); and broad multiplets from 1.3-2.8 ppm.

A solution of compound xxviii (89 mg) in 2 ml of anhydrous THF was treated with 1 ml of 0.5 M hydrochloric acid and allowed to stir at room temperature under a nitrogen atmosphere in a 50 ml pear-shaped flask. The reaction mixture was stirred for 2 hours at room temperature, then diluted with 50 ml of ethyl acetate and washed twice with 50 ml of brine, and dried over solid sodium sulfate. The solvents were evaporated under reduced pressure. The crude product was purified by chroma-tography on a 46×1 cm column of silica gel packed and eluted with 25:75 acetone/hexane. Pure fractions were combined to give 39 mg of the final product, compound xxvix, latanoprost 1,15-lactone (Structure VI) as a colorless, viscous oil.

Compound xxvix had an Rf of 0.61 on silica gel GCF TLC plates eluted in 40:60:1 ethyl acetate/hexane/acetic acid, which was unchanged when the acetic acid was eliminated from the TLC solvent. Visualization was with sulfuric acid/charring. When 2 mg of compound xxvix was treated for 4 hours with 1 ml of methanol and 1 ml of 1 M potassium hydroxide, the compound reverted to the more polar free acid form of latanoprost, which had an Rf of 0 in this solvent system without acetic acid, an Rf of 0.21 in 40:60:1 ethyl acetate/hexane/acetic acid, and co-migrated with an authentic standard of latanoprost prepared by an alternative total synthesis. The product was dissolved in deutero-chloroform and an nmr (300 MHz-Bruker) was run, revealing a multiplet at 7.2-7.3 ppm (5H); a broad multiplet at 5.1-5.45 ppm (3H); a multiplet from 3.6-4.2 ppm (3H); and broad multiplets from 0.9-2.8 ppm (29H). A mass spectrum run on the Finnegan LCQ mass spectrometer showed a molecular ion at m/e 373.0, and loss of $H_2O$ (355.1) and $2 \times H_2O$ (337.2).

Experimental Results

The ocular antihypertensive activity of $PGF_{2\alpha}$ analogs, including fluprostenol, is known to science. However, the ability of corneal esterases to act on the novel 1,15-lactones of 16- and 17-aryl-substituted analogs of $PGF_{2\alpha}$, thereby releasing the active free acid has not been shown. We therefore tested and documented the ability of corneal esterases to utilize fluprostenol 1,15-lactone (Structure IV; Example 1, compound xvi) as a substrate.

Enzymatic hydrolysis of fluprostenol 1,15-lactone by corneal esterase enzymes was documented by suspending 500 μg of fluprostenol 1,15-lactone in 10 ml of pH 7.4 phosphate buffered saline containing approximately 40 mg of freshly collected bovine corneal tissue. The mixture was incubated at 37° C. and analyzed at 2 hour, 4 hour and 18 hour time intervals by Thin Layer Chromatography (TLC; Analtech silica gel G-60 plates) using 40:60 acetone:dichloromethane containing 0.5% acetic acid. The plates were visualized by spraying with vanillin dissolved in methanol and phosphoric acid; followed by charring on a hot plate. $PGF_{2\alpha}$ methyl ester, which is known to be hydrolyzed by corneal esterases, was subjected to the same procedure as a control.

Figure 3C:
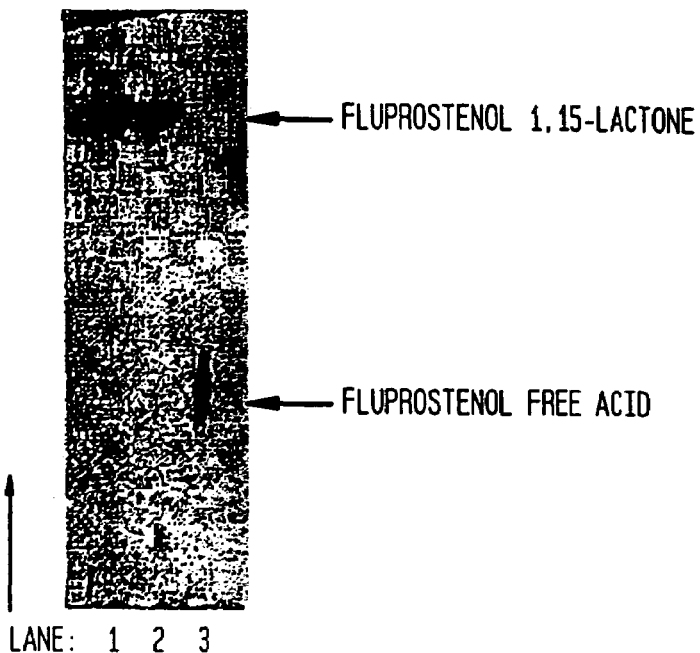
Figure 3D:
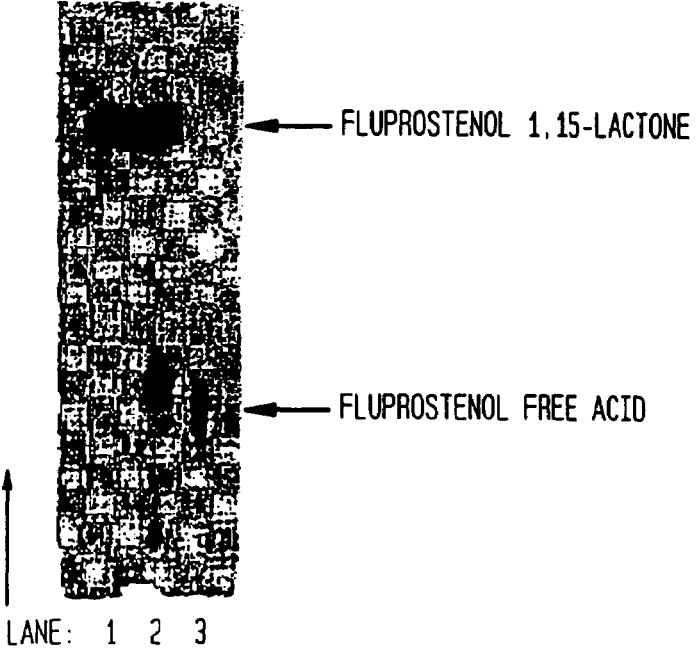

The results are shown in FIGS. 3A-3D which are images of chromatography plates developed at 2 hours (FIGS. 3A and 3C) and 4 hours (FIGS. 3B and 3D), respectively. Referring to FIGS. 3A and 3B, lane 1 is the $PGF_{2\alpha}$ methyl ester standard, lane 2 is the mixture of $PGF_{2\alpha}$ methyl ester and bovine corneal tissue, and lane 3 is a $PGF_{2\alpha}$ free acid standard. Referring to FIGS. 3C and 3D, lane 1 is the fluprostenol 1,15-lactone standard, lane 2 is the mixture of fluprostenol 1,15-lactone and bovine corneal tissue, and lane 3 is a fluprostenol free acid standard. By 4 hours, the release of the free acid by hydrolysis of the novel fluprostenol 1,15-lactone is clearly shown (See, FIG. 3D, comparing lanes 2 and 3).

Figure 4A:
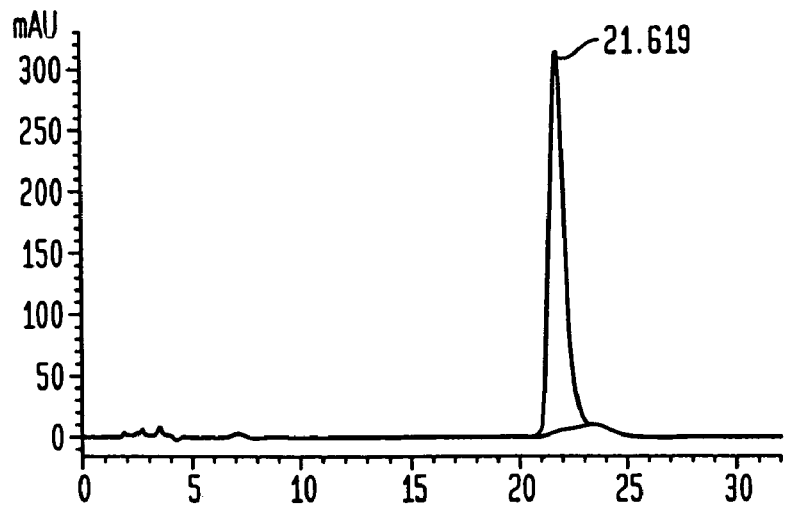
FIGS. 4A and 4B are graphic representations of High Pressure Liquid Chromatography (HPLC) analysis results for a fluprostenol 1,15-lactone standard (FIG. 4A) and a mixture of fluprostenol 1,15-lactone and bovine corneal tissue after 4 hours of incubation (FIG. 4B).
Figure 4B:
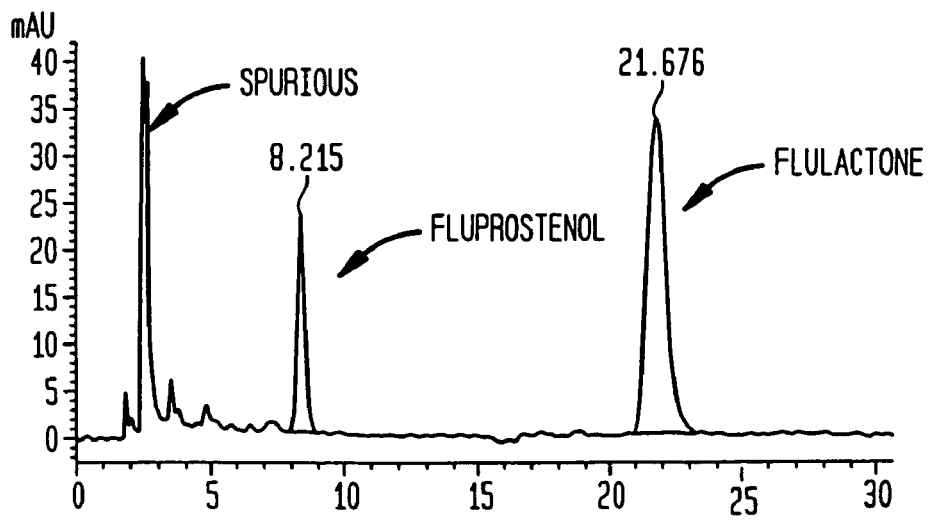

The mixture of fluprostenol 1,15-lactone and bovine corneal tissue was also analyzed using HPLC under the conditions specified in FIGS. 4A and 4B which are graphic representations of the HPLC analysis results for a fluprostenol 1,15-lactone standard (FIG. 4A) and a mixture of fluprostenol 1,15-lactone and bovine corneal tissue incubated for 4 hours (FIG. 4B). FIG. 4B shows that the conversion of fluprostenol 1,15-lactone to fluprostenol free acid was more than 50% complete after 4 hours. This rate of enzymatic hydrolysis is similar to that obtained using Prostaglandin $F_{2\alpha}$ isopropyl ester (not shown) under the same incubation conditions as a positive control.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

What is claimed is:

1. A compound of the general formula:

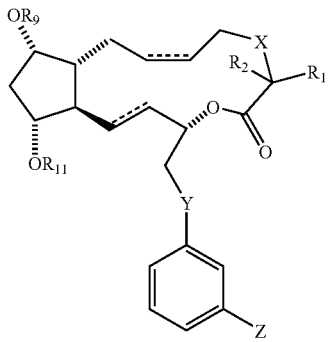

Formula I wherein X is O, S or NH;
wherein $R_1$ and $R_2$ are the same and are either H, $CH_3$ or F;
wherein $R_9$ is H, or $C_1$-$C_{20}$ straight chain, saturated or unsaturated or branched acyl;
wherein $R_{11}$ is H, or $C_1$-$C_{20}$ straight chain, saturated or unsaturated or branched acyl;
wherein — represents any combination of a single bond, or a cis or trans double bond;
wherein Z is H, Cl, Br, I, $CF_3$, $CH_3$, or $C_1$-C10 straight chain or branched alkyl; and
wherein Y is O or $CH_2$ when $R_9$ and $R_{11}$ are H and wherein X is O, S or NH;
wherein Y is O, S, NH or $CH_2$ when $R_1$ is $CH_3$ and $R_2$ is $CH_3$ or when Z is selected to be Br, I or a $C_1$-$C_{10}$ straight chain or branched alkyl.

2. The compound of claim 1 wherein $R_9$ and $R_{11}$ are H; Y is O, S, or NH; and Z is $CH_3$.

3. A compound of the general formula:

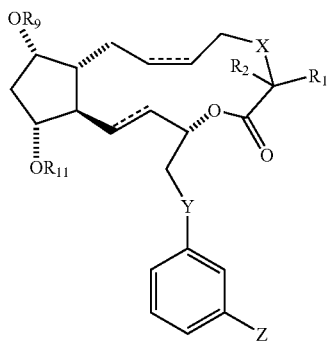

Formula I wherein X is O, S, NH or $CH_2$;
wherein $R_1$ and $R_2$ are the same and are either $CH_3$ or F;
wherein $R_9$ is H, or $C_1$-$C_{20}$ straight chain, saturated or unsaturated or branched acyl;
wherein $R_{11}$ is H, or $C_1$-$C_{20}$ straight chain, saturated or unsaturated or branched acyl;
wherein represents any combination of a single bond, or a cis or trans double bond;
wherein Z is H, Cl, Br, I, $CF_3$, $CH_3$, or $C_1$-$C_{10}$ straight chain or branched alkyl;
wherein Y is O or $CH_2$ when $R_9$ and $R_{11}$ are H and wherein X is O, S or NH; and
wherein Y is O, S, NH or $CH_2$ when $R_1$ is $CH_3$ and $R_2$ is $CH_3$ or when Z is selected to be Br, I or a $C_1$-$C_{10}$ straight chain or branched alkyl.

* * * * *

UNITED STATES PATENT AND TRADEMARK OFFICE
CERTIFICATE OF CORRECTION

PATENT NO.          : 7,358,275 B2
APPLICATION NO. : 11/353808
DATED                  : April 15, 2008
INVENTOR(S)        : Kirk M. Maxey and Michelle L. Stanton It is certified that error appears in the above-identified patent and that said Letters Patent is hereby corrected as shown below:

Claim 1, column 17, line 27 after wherein delete solid line and insert dashed (----) line Claim 1, column 17, line 29 after After $C_1$ delete "C10" and insert --$C_{10}$--

Claim 3, column 18, line 26 after wherein insert dashed (----) line

Signed and Sealed this

Seventeenth Day of March, 2009

JOHN DOLL
*Acting Director of the United States Patent and Trademark Office*